United States Patent [19]

Gesing et al.

[11] Patent Number: 5,508,441
[45] Date of Patent: Apr. 16, 1996

[54] HERBICIDAL SUBSTITUTED THIENYLSULPHONYLUREAS

[75] Inventors: Ernst R. F. Gesing, Erkrath-Hochdahl; Hans-Joachim Santel, Leverkusen; Klaus Lürssen; Robert R. Schmidt, both of Bergish Gladbach, all of Germany

[73] Assignee: Bayer Aktiengesellschaft, Leverkusen, Germany

[21] Appl. No.: 412,432

[22] Filed: Mar. 29, 1995

Related U.S. Application Data

[62] Division of Ser. No. 124,919, Sep. 21, 1993, Pat. No. 5,430,006.

[30] Foreign Application Priority Data

Sep. 28, 1992 [DE] Germany ............ 42 32 417.3

[51] Int. Cl.⁶ ............ C07D 333/34; C07D 333/32
[52] U.S. Cl. ............ 549/64; 549/69
[58] Field of Search ............ 549/64, 69

[56] References Cited

U.S. PATENT DOCUMENTS

| | | | |
|---|---|---|---|
| 4,481,029 | 11/1984 | Levitt | 504/212 |
| 4,549,898 | 10/1985 | Böhner et al. | 504/215 |
| 5,138,072 | 8/1992 | Wagner | 549/64 |

FOREIGN PATENT DOCUMENTS

| | | |
|---|---|---|
| 0030142 | 6/1981 | European Pat. Off. . |
| 0097122 | 12/1983 | European Pat. Off. . |
| 0164269 | 12/1985 | European Pat. Off. . |
| 0207609 | 1/1987 | European Pat. Off. . |
| 2159156 | 11/1985 | United Kingdom . |

OTHER PUBLICATIONS

*Chemical Abstracts, 27–Heterocycles*, p. 773, vol. 119, 1993; 180647y: "Preparation of 3–amino–2–thiophenecarboxylic Acid Derivatives", M. Ishizaki et al., Jpn. Kokai Tokkyo Koho JP 05,117,263.

*Primary Examiner*—Allen J. Robinson
*Assistant Examiner*—Mary C. Cebulak
*Attorney, Agent, or Firm*—William C. Gerstenzang; Sprung Horn Kramer & Woods

[57] ABSTRACT

Herbicidal substituted thienylsulphonylureas of the formula

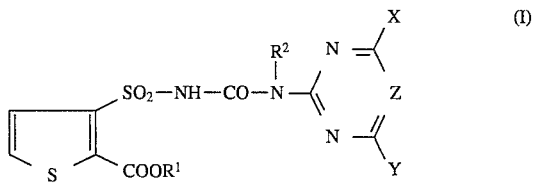

in which $R^1$ represents ethyl or n-propyl, $R^2$ represents hydrogen or methyl, X and Y are identical or different and each represent hydrogen, hydroxyl, amino, cyano, halogen, $C_1$–$C_4$-alkyl, $C_3$–$C_6$-cycloalkyl, $C_1$–$C_4$-halogenoalkyl, $C_1$–$C_4$-alkoxy-$C_1$–$C_4$-alkyl, $C_1$–$C_4$-alkoxy, $C_1$–$C_4$-halogeno-alkoxy, $C_1$–$C_4$-alkoxy-$C_1$–$C_4$-alkoxy, $C_1$–$C_4$-alkylthio, $C_1$–$C_4$-alkylamino or di-($C_1$–$C_4$-alkyl)-amino and Z represents nitrogen, a CH group or a C-halogen group, and their salts.

1 Claim, No Drawings

HERBICIDAL SUBSTITUTED THIENYLSULPHONYLUREAS

This is a divisional of application Ser. No. 08/124,919, filed on Sep. 21, 1993, now U.S. Pat. No. 5,430,006.

The invention relates to novel substituted thienylsulphonylureas, processes and novel intermediates for their preparation and their use as herbicides.

It is already known that certain substituted thienylsulphonylureas, such as, for example, N-(4-methoxy-6-methyl,- 1,3,5-triazin-2-yl)-N'-(2-methoxycarbonyl-thien-3-yl-sulphonyl)-urea (thifensulfuron-methyl), have powerful herbicidal activity (cf. EP-A 30142). However, the action of these compounds—in particular their toleration by crop plants—is not always completely satisfactory.

The novel substituted thienylsulphonylureas of the general formula (I)

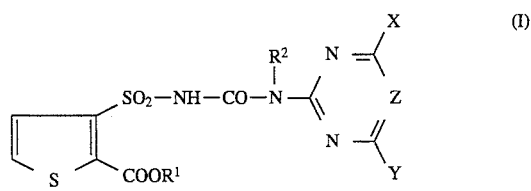

in which $R^1$ represents ethyl or n-propyl, $R^2$ represents hydrogen or methyl, X and Y are identical or different and each represents hydrogen, hydroxyl, amino, cyano, halogen, $C_1$–$C_4$-alkyl, $C_3$–$C_6$-cycloalkyl, $C_1$–$C_4$-halogenoalkyl, $C_1$–$C_4$-alkoxy-$C_1$–$C_4$-alkyl, $C_1$–$C_4$-alkoxy, $C_1$–$C_4$-halogenoalkoxy, $C_1$–$C_4$-alkoxy-$C_1$–$C_4$-alkoxy, $C_1$–$C_4$-alkylthio, $C_1$–$C_4$-alkylamino or di-($C_1$–$C_4$-alkyl)-amino and Z represents nitrogen, a CH group or a C-halogen group, and salts of compounds of the formula (I) have now been found.

The novel substituted thienylsulphonylureas of the general formula (I) are obtained when (a) thiophenesulphonamides of the general formula (II)

in which $R^1$ has the abovementioned meaning, are reacted with chloroformic esters of the general formula (III)

$$Cl-CO-O-R^3 \quad (III)$$

in which $R^3$ represents $C_1$–$C_4$-alkyl, phenyl or benzyl, optionally in the presence of an acid acceptor and optionally in the presence of a diluent, and the resulting urethanes (carbamates) of the general formula (IV)

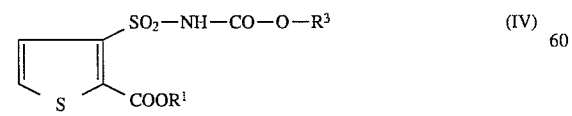

in which $R^1$ and $R^3$ have the abovementioned meaning, are reacted —optionally without intermediate isolation—with azines of the general formula (V)

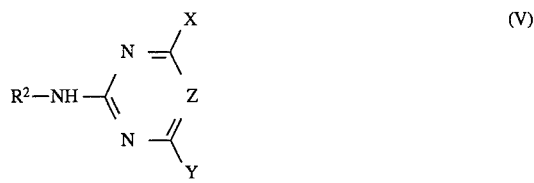

in which $R^2$, X, Y and Z have the abovementioned meaning, optionally in the presence of a reaction auxiliary, or if (b) thienylsulphonyl isocyanates of the general formula (VI)

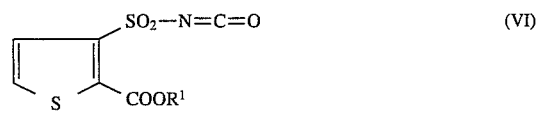

in which $R^1$ has the abovementioned meaning, are reacted with azines of the general formula (V)

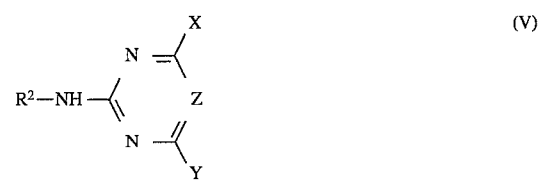

in which $R^2$, X, Y and Z have the abovementioned meanings, optionally in the presence of a diluent.

The novel substituted thienylsulphonylureas of the general formula (I) have powerful and selective activity.

Surprisingly, the novel compounds of the formula (I) exhibit very good toleration by crops, such as, for example, wheat, coupled with a much more powerful action against certain problem weeds than the thienylsulphonylureas known from the prior art.

The invention preferably relates to compounds of the formula (I) in which $R^1$ represents ethyl or n-propyl, $R^2$ represents hydrogen or methyl, X represents hydrogen, hydroxyl, amino, cyano, fluorine, chlorine, bromine, methyl, ethyl, n- or i-propyl, n-, i-, s- or t-butyl, cyclopropyl, trifluoromethyl, methoxymethyl, ethoxymethyl, methoxyethyl, ethoxyethyl, methoxy, ethoxy, n- or i-propoxy, difluoromethoxy, trifluoromethoxy, chloroethoxy, fluoroethoxy, dichloroethoxy, difluoroethoxy, trichloroethoxy, trifluoroethoxy, chlorodifluoroethoxy, methoxyethoxy, ethoxyethoxy, methylthio, ethylthio, n- or i-propylthio, methylamino, ethylamino, n- or i-propylamino, dimethylamino or diethylamino, Y represents hydrogen, hydroxyl, amino, cyano, fluorine, chlorine, bromine, methyl, ethyl, cyclopropyl, trifluoromethyl, methoxy, ethoxy, difluoromethoxy, methylthio, ethylthio, methylamino, ethylamino or dimethylamino and Z is nitrogen or a CH group.

The invention furthermore preferably relates to salts which are obtained from compounds of the formula (I) and bases, such as, for example, sodium hydroxide, potassium hydroxide or calciumhydroxide, sodium hydride, potassium hydride or calcium hydride, sodiumamide, potassiumamide or calciumamide or sodium carbonate, potassium carbonate or calcium carbonate, sodium $C_1$–$C_4$-alkanolates or potassium $C_1$–$C_4$-alkanolates, ammonia, $C_1$–$C_4$-alkylamines, di-($C_1$–$C_4$-alkyl)-amines or tri-($C_1$–$C_4$-alkyl)-amines.

The invention relates in particular to compounds of the formula (I), in which $R^1$ represents ethyl or n-propyl, $R^2$ represents hydrogen or methyl, X represents methyl, methoxy or methylthio, Y represents hydrogen, methyl, methoxy or methylthio and Z represents nitrogen or a CH group.

The abovementioned general definitions of radicals or explanations, or those mentioned in preferred ranges, are applicable in a corresponding manner to the end products and to the starting materials and intermediates. These definitions of radicals may be combined as desired with one another, in other words also between the particular preferred ranges.

If 2-ethoxycarbonylthiophene-3-sulphonamide and methyl chloroformate and 2-amino-4,6-dimethoxypyrimidine are used as starting materials, for example for process variant (a), the reaction sequence may be represented by the following scheme:

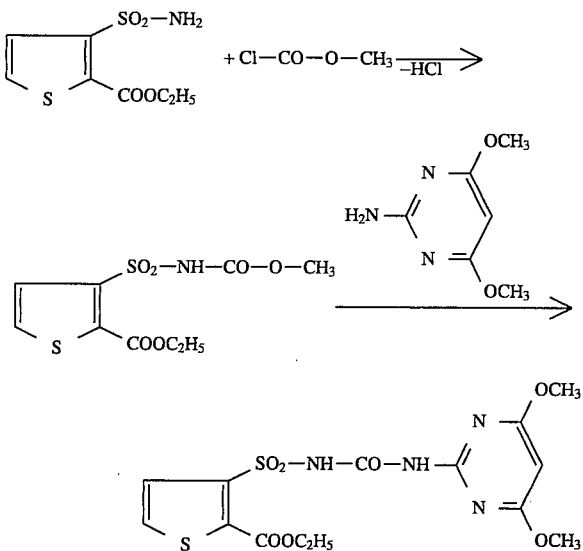

If 2-propoxycarbonyl-thiophen-3-yl-sulphonyl isocyanate and 2-methylamino-4,6-dimethoxy-s-triazine are used as starting materials, for example for process variant (b), the reaction sequence may be represented by the following scheme:

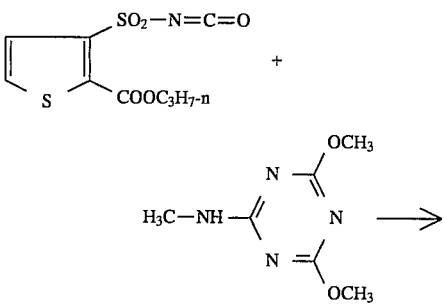

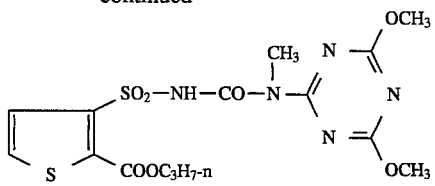

The thiophenesulphonamides—2-ethoxycarbonyl-thiophene-3-sulphonamide and 2-propoxycarbonyl-thiophene-3-sulphonamide— to be used as starting materials in the preparation process (a) according to the invention are not yet known from the literature and, as novel substances, form the subject of the present patent application.

The novel thiophenesulphonamides of the formula (II) are obtained when corresponding thiophenesulphonyl chlorides of the general formula (VII)

in which $R^1$ has the abovementioned meaning, are reacted with ammonia, optionally in the presence of a diluent, such as, for example, methylene chloride, at temperatures between –30° C. and +50° C. (cf. the Preparation Examples).

Among the thiophenesulphonyl chlorides of the formula (VII), 2-ethoxycarbonyl-thiophene-3-sulphonyl chloride is already known (cf. ES-P 556919—cited in Chem. Abstracts 109:93034w).

On the other hand, 2-propoxycarbonyl-thiophene-3-sulphonyl chloride is not yet known from the literature and, as a novel substance, forms the subject of the present patent application.

The novel 2-propoxycarbonyl-thiophene-3-sulphonyl chloride is obtained when propyl 3-amino-thiophene-2-carboxylate is reacted with sodium nitrite in the presence of hydrochloric acid at temperatures between –10° C. and +10° C. and then with sulphur dioxide in the presence of a copper catalyst, such as, for example, copper (I) chloride, and in the presence of a diluent, such as, for example, acetic acid, at temperatures between 10° C. and 50° C. (cf. the preparation examples).

The propyl 3-amino-thiophene-2-carboxylate required as an intermediate is not described in the literature and, as a novel substance, likewise forms the subject of the present patent application.

The novel propyl 3-amino-thiophene-2-carboxylate is obtained when propyl thioglycolate is reacated with 2-chloro-acrylonitrile in the presence of an acid acceptor, such as, for example, sodium propanolate, and in the presence of a diluent, such as, for example, propanol, at temperatures between 0° C. and 100° C. (cf. the preparation examples).

The chloroformic esters furthermore to be used as starting materials in process (a) according to the invention for the preparation of compounds of the formula (I) are defined generally by the formula (III).

In the formula (III), $R^3$ preferably represents methyl, ethyl, phenyl or benzyl, in particular phenyl.

The starting materials of the formula (III) are known synthetic chemicals.

The urethanes (carbamates) of the formula (IV) which are obtained as intermediates in process (a) according to the invention are not described in the literature and, as novel substances, likewise form the subject of the present patent application.

In the formula (IV), $R^1$ and $R^3$ preferably or in particular have those meanings which have already been mentioned above in connection with the description of the formula (I) or (III) as being preferred or particularly preferred for $R^1$ and $R^3$.

The azines furthermore to be used as starting materials in process (a) according to the invention for the preparation of compounds of the formula (I) are defined generally by the formula (V).

In the formula (V), $R^2$, X, Y and Z preferably or in particular have those meanings which have already been mentioned above in connection with the description of the compounds, according to the invention, of the formula (I) as being preferred or particularly preferred for $R^2$, X, Y and Z.

The starting materials of the formula (V) are known and/or can be prepared by processes known per se (cf. U.S. Pat. No. 4299960; EP-A 121082; EP-A 125205; EP-A 126711; EP-A 152378; EP-A 158594).

Process (a) according to the invention for the preparation of the novel compounds of the formula (I) is preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, as well as dimethyl sulphoxide, tetramethylene sulphone and hexamethylphosphoric acid triamide.

All acid acceptors which can usually be used for such reactions can be employed as acid acceptors in process (a) according to the invention. Alkali metal and alkaline earth metal hydrides, such as lithium hydride, sodium hydride, potassium hydride and calcium hydride, alkali metal and alkaline earth metal hydroxides, such as lithium hydroxide, sodium hydroxide, potassium hydroxide and calcium hydroxide, alkali metal and alkaline earth metal carbonates and bicarbonates, such as sodium carbonate and potassium carbonate or sodium bicarbonate and potassium bicarbonate and calcium carbonate, alkali metal acetates, such as sodium acetate and potassium acetate, alkali metal alcoholates, such as sodium methylate and potassium methylate, sodium ethylate and potassium ethylate, sodium propylate and potassiumpropylate, sodium isopropylate and potassium isopropylate, sodium butylate and potassium butylate, sodium isobutylate and potassium isobutylate and sodium tert-butylate and potassium tert-butylate, and furthermore basic nitrogen compounds, such as trimethylamine and triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo[4.3.0]non-5-ene (DBN), 1,8-diazabicyclo[5.4.0]undec-7-ene (DBU) and 1,4-diazabicyclo[2.2.2]octane (DABCO), are preferred.

The second reaction phase of the process according to the invention, that is to say the reaction with the azines of the formula (V), is preferably carried out in the presence of a reaction auxiliary. Preferably used reaction auxiliaries here are acids, in particular protic acids, such as sulphuric acid, methanesulphonic acid, benzene-sulphonic acid and p-toluenesulphonic acid.

In process (a) according to the invention, the reaction temperatures can be varied within a relatively large range. In general, temperatures between 0° C. and 150° C., preferably temperatures between 10 ° C. and 100 ° C., are employed.

Process (a) according to the invention is carried out in general under atmospheric pressure. However, it is also possible to employ elevated or reduced pressures.

To carry out process (a) according to the invention, the particular starting materials required are used in general in approximately equimolar amounts. However, it is also possible to use one or more of the particular components used in a relatively large excess.

The thiophenesulphonamides of the formula (II) are preferably first reacted with chloroformic esters of the formula (III), and the resulting urethanes of the formula (IV) are then reacted with the azines of the formula (V), without intermediate isolation. The reaction mixture is then stirred, in general at elevated temperature, to the end of the reaction and is then worked up in a customary manner (cf. the Preparation Examples).

The thienylsulphonyl isocyanates—2-ethoxycarbonylthien-3-ylsulphonyl isocyanate and 2-propoxycarbonylthein-3-ylsulphonyl isocyanate—to be used as starting materials in preparation process (b) according to the invention are not described in the literature and, as novel substances, form the subject of the present patent application.

The novel thienyl sulphonyl isocyanates of the formula (VI) are obtained when corresponding thiophenesulphonamides of the general formula (II)

in which $R^1$ has the abovementioned meaning, are reacted with phosgene, preferably in the presence of an alkyl isocyanate, such as, for example, butyl isocyanate, in the presence of a reaction auxiliary, such as, for example, diazabicyclo[2.2.2]octane, and in the presence of a diluent, such as, for example, xylene, at temperatures between 100° C. and 150° C., and, after the end of the reaction, the volatile components are distilled off under reduced pressure.

Process (b) according to the invention is furthermore carried out with the use of azines of the general formula (V). Statements made above with regard to the azines of the formula (V) in the description of the starting materials for process (a) according to the invention are applicable here.

Process (b) according to the invention is preferably carried out using a diluent. Those organic solvents which were mentioned above for process (a) according to the invention are preferred here.

To carry out process (b) according to the invention, the particular starting materials required are used in general in approximately equimolar amounts. However, it is also possible to use one of the two components used in each case in a relatively large excess. The reactions are carried out in general in a suitable diluent, and the reaction mixture is stirred for several hours at the temperature required in each case. In process (b) according to the invention, working up is carried out in each case by customary methods (cf. the Preparation Examples).

If desired, salts may be prepared from the compounds, according to the invention, of the general formula (I). Such salts are obtained in a simple manner by customary salt formation methods, for example by dissolving or dispersing a compound of the formula (I) in a suitable diluent, such as, for example, methylene chloride, acetone, tert-butyl methyl ether or toluene, and adding a suitable base. The salts can then be isolated by evaporation or filtration under suction—optionally after prolonged stirring.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Impomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotvledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land and for the selective combating of weeds in annual cultures.

The compounds according to the invention of the formula (I) are suitable in particular for selectively combating monocotyledon and dicotyledon weeds in monocotyledon cultures, both by the preemergence method and by the postemergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If water is used as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients .such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugarbeet and 4-amino-6-(1,1-dimethylethyl)-3-methylthio-1,2,4-triazin- 5(4H)-one for combating weeds in soya beans. Surprisingly, some mixtures also show a synergistic effect.

Similarly, a mixture with known active compounds such as fungicides, insecticide, acaricides, nematicides, bird repellents, plant nutrient, and soil structure improvers is possible.

The active compounds can be used as such, in the form of their formulations or in the use forms prepared therefrom by further dilution, such as ready-to-use solutions, suspensions, emulsions, powders, pastes or granules. They are applied in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLE

Example 1

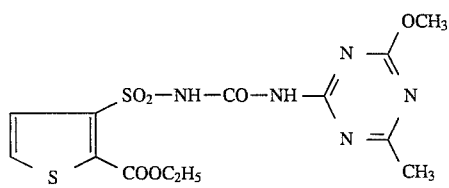

(Process(a))

2.34 g (15 mmol) of phenyl chloroformate are added to a mixture of 3.53 g (15 mmol) of 2-ethoxycarbonylthiophene-3-sulphonamide, 3.03 g (30 mmol) of triethylamine and 60 ml of acetonitrile at 10° C. to 20° C. while stirring. After stirring for thirty minutes, 1.44 g (15 mmol) of methanesulphonic acid and 2.10 g (15 mmol) of 2-amino-4-methoxy-6-methyl-s-triazine are added in succession to the mixture. The reaction mixture is heated under reflux for 30 minutes. It is then evaporated down under a vacuum from a water pump, and the residue is thoroughly shaken with water/methylene chloride. The organic phase is separated off, dried with sodium sulphate and filtered. The filtrate is evaporated down, the residue is stirred with diethyl ether and the crystalline product is isolated by filtration under suction.

3.4 g (57% of theory) of N-(4-methoxy-6-methyl-s-triazin-2-yl)-N'-(2-ethoxycarbonyl-thien-3-yl-sulphonyl)-urea of melting point 166° C. are obtained.

EXAMPLE 2

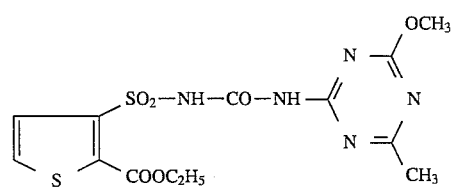

(Process (b))

A mixture of 7.7 g (55 mmol) of 2-amino-4-methoxy-6-methyl-s-triazine, 14.4 g (55 mmol) of 2-ethoxycarbonylthiein-3-yl-sulphonyl isocyanate and 100 ml of acetonitrile is heated under reflux for 4 hours and then cooled slowly to 20° C. The product which separates out in crystalline form is isolated by filtration under suction.

15.6 g (71% of theory) of N-( 4-methoxy-6-methyl-s-triazin-2-yl)-N' -(2-ethoxycarbonyl-thien-3-yl-sulphonyl )urea of melting point 166° C. are obtained.

For example, the compounds of the formula (I) which are mentioned in Table 1 below can also be prepared analogously to Examples 1 and 2 and according to the general description of the preparation processes according to the invention.

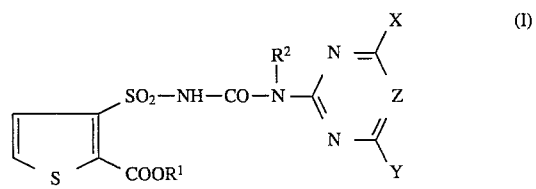

TABLE 1

Examples of the compounds of the formula (I)

| Example No. | $R^1$ | $R^2$ | X | Y | Z | Melting point (°C.) |
|---|---|---|---|---|---|---|
| 3 | $C_2H_5$ | H | $OCH_3$ | H | N | 203 |
| 4 | $C_2H_5$ | H | $OCH_3$ | $OCH_3$ | N | 180 |
| 5 | $C_2H_5$ | H | $OCH_3$ | $OCH_3$ | CH | 153 |
| 6 | $C_2H_5$ | H | $OCH_3$ | ◁ | N | 173 |
| 7 | $C_2H_5$ | H | $SCH_3$ | ◁ | N | 143 |
| 8 | $C_2H_5$ | H | $i\text{-}C_3H_7$ | $SCH_3$ | N | 143 |
| 9 | $n\text{-}C_3H_7$ | H | $OCH_3$ | $CH_3$ | N | 155 |
| 10 | $n\text{-}C_3H_7$ | H | $OCH_3$ | $CH_3$ | CH | 153 |
| 11 | $n\text{-}C_3H_7$ | H | $OCH_3$ | H | N | 187 |
| 12 | $n\text{-}C_3H_7$ | H | $OCH_3$ | $OCH_3$ | N | 162 |
| 13 | $C_2H_5$ | H | $CH_3$ | $CH_3$ | N | 196 |
| 14 | $C_2H_5$ | H | $SCH_3$ | $CH_3$ | N | 184 |
| 15 | $n\text{-}C_3H_7$ | H | $CH_3$ | $CH_3$ | N | 169 |
| 16 | $n\text{-}C_3H_7$ | H | $SCH_3$ | $CH_3$ | N | 173 |
| 17 | $n\text{-}C_3H_7$ | H | $CH_3$ | $CH_3$ | CH | 159 |
| 18 | $n\text{-}C_3H_7$ | H | $CH_3$ | H | CH | 186 |
| 19 | $n\text{-}C_3H_7$ | H | $OCH_3$ | $OCH_3$ | CH | 132 |
| 20 | $C_2H_5$ | H | $OCH_3$ | $CH_3$ | CH | 182 |
| 21 | $C_2H_5$ | H | $CH_3$ | $CH_3$ | CH | 166 |
| 22 | $C_2H_5$ | H | $CH_3$ | H | CH | 188 |
| 23 | $C_2H_5$ | $CH_3$ | $OCH_3$ | $CH_3$ | N | 137 |
| 24 | $C_2H_5$ | $CH_3$ | $OCH_3$ | $OCH_3$ | N | 138 |
| 25 | $C_2H_5$ | H | $OCH_3$ | $CH_3$ | N | 200 (Na salt) |
| 26 | $C_2H_5$ | H | $t\text{-}C_4H_9$ | H | CH | 185 |
| 27 | $C_2H_5$ | H | $OCH_3$ | $CH_3$ | N | 149 |
| 28 | $C_2H_5$ | H | $OCH_3$ | $C_2H_5$ | N | 173 |
| 29 | $C_2H_5$ | H | $CH_3$ | $C_2H_5$ | CH | 207 |
| 30 | $C_2H_5$ | H | $i\text{-}C_4H_9$ | H | CH | 176 |
| 31 | $C_2H_5$ | H | $t\text{-}C_4H_9$ | $SCH_3$ | N | 195 |
| 32 | $C_2H_5$ | H | $SCH_3$ | $N(CH_3)_2$ | N | 165 |
| 33 | $C_2H_5$ | H | $t\text{-}C_4H_9$ | OH | N | 250 |
| 34 | $C_2H_5$ | $CH_3$ | CN | $OCH_3$ | N | 139 |
| 35 | $n\text{-}C_3H_7$ | $CH_3$ | $OCH_3$ | $CH_3$ | N | |
| 36 | $n\text{-}C_3H_7$ | $CH_3$ | $OCH_3$ | $OCH_3$ | N | |
| 37 | $C_2H_5$ | H | $CH_3$ | $N(CH_3)_2$ | N | 143 |
| 38 | $C_2H_5$ | H | $t\text{-}C_4H_9$ | $OCH_3$ | N | |
| 39 | $C_2H_5$ | H | $OCH_3$ | $N(CH_3)_2$ | N | |
| 40 | $C_2H_5$ | H | CN | $OCH_3$ | N | |
| 41 | $C_2H_5$ | H | Cl | Cl | CH | 176 |
| 42 | $C_2H_5$ | H | $OCH_3$ | Cl | CH | |
| 43 | $C_2H_5$ | H | Cl | $OCH_3$ | CH | |
| 44 | $C_2H_5$ | H | $OCH_3$ | H | CH | |
| 45 | $C_2H_5$ | H | H | H | CCl | |

The intermediates mentioned above as novel compounds can be represented by the following formulae:

The formula (IX)

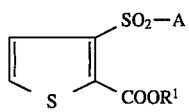 (IX)

in which

A represents $NH_2$, $NH—CO—O—R^3$ or $N+C=O$, $R^1$ represents ethyl or n-propyl and $R^3$ represents $C_1-C_4$-alkyl, phenyl or benzyl, represents the thiophene derivatives of the above formulae (II), (IV) and (VI).

The formula (X)

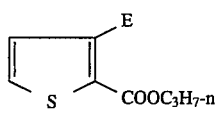 (X)

in which

E represents $NH_2$ or $SO_2Cl$, represents the thiophene derivatives of the formulae (VIII-1) and (VII-1).

Starting materials of the formula (II):

Examples (II-1)

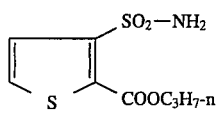 (II-1)

46 g of ammonia are passed into a solution cooled to 0° C. to 10° C. and consisting of 50 g (187 mmol) of 2-propoxy-carbonyl-thiophene-3 -sulphonyl chloride in 500 ml of methylene chloride, while stirring. The reaction mixture is stirred for 15 hours at 20° C. and then filtered. The filtrate is evaporated down, the residue is stirred with diethyl ether and the product obtained in crystalline form is isolated by filtration under suction.

31 g (67% of theory) of 2-propoxycarbonyl-thiophene-3-sulphonamide of melting point 79° C. are obtained.

Example (II-2)

2 -Ethoxycarbonyl-thiophene-3-sulphonamide of melting point 136° C. is also obtained analogously.

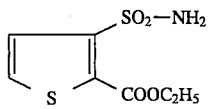 (II-2)

Starting materials of the formula (VII):

Example (VII-1)

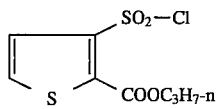 (VII-1)

A solution of 76 g (1.10 mol) of sodium nitrite in 140 ml of water is added dropwise to a solution of 185 g (1.00 mol) of propyl 3-amino-thiophene-2-carboxylate in 630 ml of hydrochloric acid at −5° C. to 0° C. in the course of 60 minutes. The mixture is stirred for a further 60 minutes at 0° C. and then added dropwise at 15° C. to a solution of 600 g of sulphur dioxide in 1200 ml of acetic acid, to which 115 ml of a saturated aqueous solution of copper (I) chloride have been added beforehand. The reaction mixture is then stirred for 15 hours at 20° C., then diluted to about twice the volume with ice water and extracted twice with methylene chloride. The combined organic extraction solutions are dried with sodium sulphate and filtered. The solvent is carefully distilled off from the filtrate in a vacuum from a water pump.

205 g (76% of theory) of 2-propoxycarbonyl-thiophene-3-sulphonyl chloride are obtained as an oily residue, which can be used for the next reaction stage without further purification.

Example (VII-2)

2-Ethoxycarbonyl-thiophene-3-sulphonyl chloride is also obtained analogously

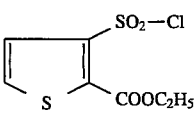 (VII-2)

Preparation of propyl 3-amino-thiophene-2-carboxylate:

Example (VIII-1)

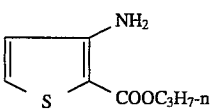 (VIII-1)

A sodium propylate solution is prepared by reacting 2.6 g (113 mmol) of sodium with propanol (100 ml) at 50° C. A solution of 6.7 g (50 mmol) of n-propyl thioglycolate in 20 ml of propanol is added dropwise to this solution at 20° C., and a solution of 4.4 g (50 mmol) of 2-chloroacrylonitrile in 20 ml of propanol is then metered in at 25° C. to 30° C. (external cooling required). The reaction mixture is stirred for 20 hours at 20° C., then evaporated down to about ⅓ of the volume, then diluted with 100 ml of water and extracted three times with in each case 100 ml of diethyl ether. The combined organic extraction solutions are washed with water, dried with sodium sulphate and filtered. The solvent is carefully distilled off from the filtrate under a vacuum from a water pump.

5 g ( 54% of theory) of propyl 3-amino-thiophene-2-carboxylate are obtained as an oily residue, which can be directly reacted further.

Use Examples

In the following use examples, the compound shown below is used as the comparative substance:

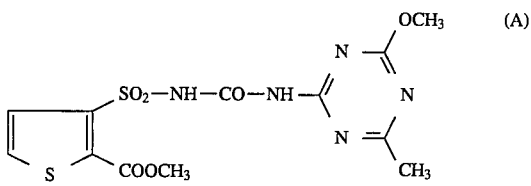 (A)

N-(4-Methoxy-6-methyl-1,3,5,-triazin-2-yl)-N'-(2 -methoxycarbonyl-thien-3-yl-sulphonyl )-urea (thifensulfuronmethyl)

(Disclosed in EP-A 30142).

Example A

Preemergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep the amount of water per unit area constant. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example, the compounds according to Preparation Example 1, 4, 9, 10, 12, 14, 16, 17, 19, 20, 21, 22 and 23 exhibit a very powerful action against weeds coupled with, in some cases, very good toleration by crop plants, e.g. such as wheat. Herein the compound according to Example 28 proved to be particularly useful.

Example B

Postemergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

The figures denote:

0%=no action (like untreated control)

100%=total destruction

In this test, for example, the compounds according to Preparation Example 1, 3, 4, 5, 9, 10, 12, 13, 14, 17, 19, 20, 21, 22 and 23 exhibit a very powerful action against weeds coupled with, in all cases, very good toleration by crop plants, such as, for example, wheat. Herein again, the compound of Example 28 acts in a very similar way.

It will be appreciated that the instant specification and claims are set forth by way of illustration and not limitation, and that various modifications and changes may be made without departing from the spirit and scope of the present invention.

We claim:

1. A thiophene derivative of the formula

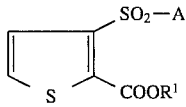

(IX)

in which

A represents $NH_2$, $NH-CO-O-R^3$ or $N=C=O$, $R^1$ represents ethyl or n-propyl and $R^3$ represents $C_1-C_4$-alkyl, phenyl or benzyl.

* * * * *